United States Patent
Kojima

(10) Patent No.: US 11,885,756 B2
(45) Date of Patent: Jan. 30, 2024

(54) METHOD FOR EXAMINING BIOLOGICAL FLUID

(71) Applicant: Yoshitane Kojima, Osaka (JP)

(72) Inventor: Yoshitane Kojima, Osaka (JP)

(73) Assignee: Yoshitane Kojima, Osaka (JP)

( * ) Notice: Subject to any disclaimer, the term of this patent is extended or adjusted under 35 U.S.C. 154(b) by 517 days.

(21) Appl. No.: 17/273,155

(22) PCT Filed: Aug. 22, 2019

(86) PCT No.: PCT/JP2019/032728
§ 371 (c)(1),
(2) Date: Mar. 3, 2021

(87) PCT Pub. No.: WO2020/059401
PCT Pub. Date: Mar. 26, 2020

(65) Prior Publication Data
US 2021/0325322 A1    Oct. 21, 2021

(30) Foreign Application Priority Data
Sep. 21, 2018   (JP) .................................. 2018-176762

(51) Int. Cl.
*G01N 23/223* (2006.01)
*G01N 33/84* (2006.01)
*G01N 33/487* (2006.01)

(52) U.S. Cl.
CPC ......... *G01N 23/223* (2013.01); *G01N 33/487* (2013.01); *G01N 33/84* (2013.01)

(58) Field of Classification Search
CPC .... G01N 23/223; G01N 33/487; G01N 33/84; G01N 33/6815
See application file for complete search history.

(56) References Cited

U.S. PATENT DOCUMENTS

2016/0084778 A1    3/2016 Kojima et al.
2020/0278346 A1*   9/2020 Zahler .............. G01N 33/54373

FOREIGN PATENT DOCUMENTS

JP    2011-107113    6/2011
JP    2012-098097    5/2012
(Continued)

OTHER PUBLICATIONS

Rompel et al., Sulfur K-edge x-ray absorption spectroscopy: a spectroscopic tool to examine the redox state of S-Containing metabolites in vivo., May 1998, Proc.Natl.Acad.Sci.USA, vol. 95, pp. 6122-61227. (Year: 1998).*

(Continued)

*Primary Examiner* — Christine S. Kim
(74) *Attorney, Agent, or Firm* — WENDEROTH, LIND & PONACK, L.L.P.

(57) ABSTRACT

A method for examining a biological fluid whereby quantitative examinations of various minerals and methionine, one of essential amino acids, contained in a biological fluid can be conducted simply, accurately, and at a low price is provided, wherein using an X-ray fluorescence analysis device, content ratios of minerals contained in a biological fluid of a subject which can be taken by the subject to sulfur originating in methionine contained therein are measured, contents of the sulfur and the minerals contained therein are calculated using the measured content ratios and calibration curves previously prepared by X-ray fluorescence analysis of standard solutions of the sulfur and the minerals, and a content of the methionine contained therein is calculated on the basis of the calculated content of the sulfur.

7 Claims, 6 Drawing Sheets

(56) References Cited

FOREIGN PATENT DOCUMENTS

| JP | 2013-221866 | 10/2013 | | |
|---|---|---|---|---|
| JP | 2016-038335 | 3/2016 | | |
| WO | WO-2008127291 A2 * | 10/2008 | ......... | G01N 23/2204 |
| WO | 2014/132383 | 9/2014 | | |
| WO | 2015/060317 | 4/2015 | | |

OTHER PUBLICATIONS

Pushie et al., Elemental and Chemically Specific X-ray Fluorescence Imaging of Biological Systems, Aug. 7, 2014, Chem. Rev. vol., 114, pp. 8499-8541. (Year: 2014).*
International Search Report, dated Nov. 19, 2019 in corresponding International Patent Application No. PCT/JP2019/032728.
Pinkerton et al., "Determination of Forms of Sulphur in Plant Material by X-Ray Fluorescence Spectrometry", X-Ray Spectrometry, vol. 19: 63-65 (1990)
Ohta et al., "Quantitative of sulfur-containing amino acids and proteins by method of energy dispersive X-ray fluorescence analysis", Advances in X-ray Chemical Analysis, vol. 18: 105-118 (1983)

* cited by examiner

Fig. 13

Reference of Mineral Nutrition

Report of Mineral Examination Results by a Hair and a Drop of Blood

Measurement Date: year/month/day

Name: Mr./Ms.

[Examination Results by Blood]
[Essential Minerals]

| Mineral | Measurement Value (ppm) | Reference Values (ppm) | Low | Reference | High |
|---|---|---|---|---|---|
| Mg Magnesium | 15 | 16 - 23 | ▓▓▓▓ | | |
| P Phosphorus | 69 | 111 - 213 | ▓▓▓ | | |
| Cl Chlorine | 705 | 420 - 494 | ▓▓▓▓ | ▓▓▓▓ | ▓▓▓ |
| K Potassium | 70 | 86 - 126 | ▓▓▓▓ | | |
| Fe Iron | 14 | 21 - 31 | ▓▓ | | |
| Cu Copper | 0.68 | 0.47 - 0.68 | ▓▓▓▓ | ▓▓▓▓ | |
| Zn Zinc | 2.73 | 2.21 - 3.02 | ▓▓▓▓ | ▓▓▓ | |
| Ge Germanium | 0.19 | 0.20 - 0.40 | ▓▓▓▓ | | |

The contents of minerals (magnesium, phosphorus, chlorine, potassium, iron, copper, zinc) in your blood each were evaluated. As to the minerals whose contents are lower than their reference values, please improve the intake shortage of them and pay attention to the intake of them.

[Examination Results by Hair]

| Mineral | Measurement Value (ppm) | Reference Values (ppm) | Low | Reference | High |
|---|---|---|---|---|---|
| Ca Calcium | 2.10 | 1.70 - 2.90 | ▓▓▓▓ | ▓▓ | |
| Cu Copper | 0.31 | 0.30 - 0.36 | ▓▓▓▓ | ▓ | |
| Zn Zinc | 2.87 | 2.93 - 3.13 | ▓▓▓▓ | | |
| Ge Germanium | 0.27 | 0.20 - 0.40 | ▓▓▓▓ | ▓▓ | |

The contents of minerals (calcium, zinc, and copper) in your hair each were evaluated.
As to the essential minerals whose contents are lower than their reference values, please improve the intake shortage of them and pay attention to the intake of them.
If the content of calcium is high, there is a fear of shortage of calcium in your body, leading to a loss of calcium in the bone. This is known as the calcium paradox.

[Examination Results by Hair: Toxic Element]

| Mineral | Measurement Value (ppm) | Reference Values (ppm) | No Intake | Requiring Care | Requiring Discharge |
|---|---|---|---|---|---|
| Pb Lead | 0.04 | < 1.2 | ▓ | | |

As to the above mineral, if your level is the requiring care or requiring discharge, please be careful about an intake of the harmful mineral through food and the like, and aim at discharging it with dietary fiber and the like. No mercury was detected in the examinations of several hundreds of subjects.

[About the Examination Results]
In this examination, minerals in your body are simply and speedily examined using a hair and/or a drop of blood by our original technique (an X-ray fluorescence analysis device), and any number of reexaminations can be conducted. This method is precise and environment friendly (generating no waste fluid).

In the case of ICP-MS (an inductively coupled plasma mass spectrometry device), a large number of hairs (about 120 hairs) are required. Since it is difficult to cleanse them and no reexamination can be conducted, iron or else which is not discharged in hairs is detected because of contamination at all times.

These examination results numerically express concentrations of minerals contained in your blood and hair, and do not confirm the outbreak and progress of your illness, or your lifestyle improvement method.

METHOD FOR EXAMINING BIOLOGICAL FLUID

TECHNICAL FIELD

The present invention relates to a method for examining a biological fluid, and more particularly, to a method for examining a biological fluid in order to grasp the state of health of a subject by conducting a quantitative analysis of elements contained in a biological fluid of the subject using an X-ray fluorescence analysis device.

BACKGROUND ART

The mineral is one of the five major nutrients essential to the human, a material constituting tissues of the body, and also a micronutrient which acts to maintain and regulate functions of the body. Since the mineral cannot be produced in the human body, it needs to be taken in through food or supplements.

The mineral accounts for about 4% of the body. Among the mineral, mineral elements which have proved to be essential as nutrients because shortages thereof in the body are detrimental to one's health are called essential minerals. Thirteen kinds of essential minerals are now shown in the dietary reference intakes (the 2015 edition). Among them, minerals which are present in the body in large amounts are called major minerals, while minerals which are present therein in small amounts are called trace minerals. The major minerals include sodium, potassium, calcium, magnesium, and phosphorus, while the trace minerals include iron, copper, zinc, iodine, selenium, chromium, manganese, molybdenum, and cobalt.

In recent years, it has been known that the toxicity of organogermanium compounds is lower than tin or lead belonging to the same group. And as a medicinal action of germanium, it was found for the first time in 1964 that alkylates of germanium act to inhibit the growth of bacteria or fungi. Thereafter, germanium compounds having an antitumor action or an anti-malaria action began to be synthetically prepared.

In 1978, a high molecular compound having a cyclic compound containing germanium, propagermanium (calboxyethylgermanium sesquioxide) was synthetically prepared. It has been concluded that this compound excludes viruses by activating the immunity function of a host for them when an infection occurs, and further that it inhibits the proliferation of viruses by promoting the production of interferon. Even if this compound is orally administered, it stably keeps its structure under the in vivo environment to exert its effect, and it is discharged into urine as it is (Non-Patent Document 1).

As necessary minerals other than the above-stated minerals, sulfur, cobalt, fluorine, and chlorine are named, but these are not prescribed in the dietary reference intakes. That is because, since these minerals are contained in other nutrients such as amino acids, proteins, or vitamins, they can be taken in simultaneously with the other nutrients by indicating the references of the other nutrients.

Since the intake of too large or too small an amount of mineral is not desirable for the maintenance and promotion of health, well-balanced intake thereof is needed. Therefore, it is useful to make it possible to grasp a state such as excess and shortage of intakes of minerals.

In recent years, hair mineral examinations wherein the state of excess and shortage of intakes of minerals, or the state of accumulation of harmful minerals is estimated on the basis of examinations of the amounts of minerals in hair have been conducted. The hair mineral examination method most frequently conducted on the market at present is the inductively coupled plasma mass spectrometry (also referred to as ICP-MS). Since the inductively coupled plasma mass spectrometry has high sensitivity of ppb (a billionth), a sophisticated facility such as a clean room is required in order to make full use of the sensitivity. And in order to prepare a sample for measurement, a large number of hairs, for example, about 120 hairs (0.1 g or more) are required, and complicated pretreatments such as a treatment wherein the hairs are dissolved using an acid and the like are needed. In addition, since the prepared sample is used up on a single occasion, the accuracy of the examination cannot be checked thereafter.

It is extremely difficult to remove impurities adhering to 120 hairs by cleansing in the pretreatment stage. The results in which magnesium or iron, naturally not contained (discharged) in hairs, was detected and measured, have been continuously reported. According to the study of the inventors of the present invention, it was confirmed that, in the mineral examination using a single hair by X-ray fluorescence analysis, magnesium and iron of the order of ppm were not detected.

In the below-mentioned Patent Document 1, "a method for examining an element in a living body, wherein a signal ratio $P_{XRF}$ (S) of a mineral contained in hair of a subject to sulfur contained in the hair is measured by X-ray fluorescence analysis, and in order to calculate an element content ratio $M_{XRF}$ of the mineral contained in the hair from the signal ratio $P_{XRF}$ (S), the signal ratio $P_{XRF}$ (S) is multiplied by a conversion factor F used for this calculation" is disclosed.

In the below-mentioned Patent Document 2, "a method for examining a metal element in a living body, wherein a content ratio and a content of a mineral metal or a heavy metal contained in a biological fluid consisting of blood, urine, tear, perspiration, or saliva of a subject are measured by X-ray fluorescence analysis, and when the content ratio and/or the content thereof exceeds its normal value, it is judged that the amount of the mineral metal or heavy metal in the living body is abnormal" is disclosed.

In the below-mentioned Patent Document 3, "a method for examining a neurodegenerative disease, wherein the homocysteic acid concentration in urine collected from an animal subject, the homocysteic acid concentration in blood collected from the animal subject, and the homocysteine and/or methionine concentration in the same blood are measured" is disclosed.

In the below-mentioned Non-Patent Document 2, a study result of comparison between a method for determining the form of sulfur in a plant by X-ray fluorescence analysis and a method for determining the form of sulfur in a plant by chemical analysis is disclosed.

Problems to be Solved by the Invention

The determination of elements using the atomic absorption method, absorptiometry, neutron activation analysis method, or ICP-MS method which have been used in the conventional hair mineral examinations, requires advanced techniques for complicated pretreatments of samples or sample preparation. Consequently, if the technicians do not have these advanced techniques, it is difficult to obtain accurate data. In addition, time and cost are required for the pretreatments. Furthermore, in order to avoid contamination, a clean room and the like, which is an expensive facility, needs to be set up.

As a nutrient important to the human, the amino acid is named, other than the mineral.

The Patent Documents 1 and 2 describe that a content ratio of a mineral contained in hair, and a content ratio and/or a content of a mineral metal contained in a biological fluid, respectively, are measured by X-ray fluorescence analysis. However, in the Patent Documents 1 and 2, there is neither description nor suggestion about a technical idea of detecting a content of an amino acid from the result of the element analysis by X-ray fluorescence analysis, as well as the content of a mineral in those biological samples.

In the method described in the Patent Document 1, a signal ratio $P_{XRF}$ (S) of a mineral contained in hair of a subject to sulfur contained therein is measured by X-ray fluorescence analysis. The sulfur contained in the hair originates in keratin which is a protein constituting the hair.

Keratin contains many disulfide linkages (S—S linkages) originating in cystine, but the structure of keratin in which a plurality of amino acids are linked in the form of a chain is complicated. Therefore, sulfur contained in hair cannot be used as a reference for determining a content of a specific sulfur-containing amino acid. And in a biological fluid such as blood, insoluble keratin which is a protein constituting hair is not contained.

In the Patent Document 2, a measurement result regarding a relative value of X-ray fluorescence intensity of calcium to sulfur in hair is described, but it is not measured as an absolute value, and there is no evaluation as a test by the element content. And in the embodiment, there is no description about a measurement method or a measurement result regarding biological samples other than the hair.

In the above-described Patent Documents 1 and 2, there is no description suggesting which element contained in a biological fluid should be selected as a reference element of the internal standard, when conducting a quantitative analysis of an element contained in the biological fluid by X-ray fluorescence analysis.

In the Patent Document 3, as a method for measuring a methionine concentration in blood, a method using a kit adopting the immunochromatography method, and a method using a kit adopting the ELISA (Enzyme-Linked ImmunoSorbent Assay) method are disclosed. These methods require time and cost for preparation of an antigen, preparation of an antibody and the like, used for the kits. To begin with, in the invention described in the Patent Document 3, it is impossible to grasp a content of an amino acid, as well as a content of a mineral.

In the Non-Patent Document 2, it is disclosed that sulfur elements contained in a sulfate, a sulfur-containing amino acid and the like in a plant are detected by X-ray fluorescence analysis so as to detect concentrations of these sulfur elements. The method described in the Non-Patent Document 2 is not a method for conducting a quantitative analysis of contents of various kinds of minerals contained in the plant, and the sample for the examination is a plant, not a biological sample. Furthermore, in the Non-Patent Document 2, as is the case with the Patent Documents 1-3, there is no description suggesting which element contained in a biological fluid should be selected as a reference element of the internal standard, when conducting a quantitative analysis of an element contained in the biological fluid by X-ray fluorescence analysis.

Hitherto, a technique by which a content of an amino acid is quantitatively grasped, as well as a content of a mineral contained in a biological sample by an element analysis of the biological sample using an X-ray fluorescence analysis device in order to grasp the state of health of a person, was not known.

PRIOR ART DOCUMENT

Patent Document

Patent Document 1: WO 2014/132383
Patent Document 2: Japanese Patent Application Laid-Open Publication No. 2012-098097
Patent Document 3: WO 2015/060317

Non-Patent Document

Non-Patent Document 1: "Organogermanium", Haruaki Hoshizaki, Kenzensha (issued in April, 2005)
Non-Patent Document 2: A. Pinkerton et al., Determination of Forms of Sulphur in Plant Material by X-ray Fluorescence Spectrometry, X-RAY SPECTROMETRY, 1990, Vol. 19, pp. 63-65

SUMMARY OF THE INVENTION

Means for Solving Problem and the Effect

For conducting a quantitative analysis of a mineral contained in a sample by X-ray fluorescence analysis, it is very important to determine which element in the sample should be selected as a reference element of the internal standard.

As described in the Patent Document 1, in the case of hair, sulfur contained in keratin constituting the hair could be adopted as a reference element of the internal standard. However, since insoluble keratin is not contained in a biological fluid such as blood, it was not clear which element should be selected as a reference in the case of the biological fluid.

According to the study of the inventors of the present invention, since it was clear that a fixed amount of calcium was contained in blood due to the calcium paradox, it was initially anticipated that a quantitative analysis of each element could be done by calculating a content of each element in blood from its content ratio to calcium, and they tried blood examinations by X-ray fluorescence analysis.

However, since the signal of calcium overlapped a signal of another element in the analysis result of blood by the X-ray fluorescence analysis, calcium could not be adopted as a reference.

On the other hand, sulfur was detected in the analysis result of blood by the X-ray fluorescence analysis, and it was found that the sulfur originated in methionine, being a soluble amino acid.

The inventors found through earnest studies that by selecting sulfur originating in methionine contained in a biological fluid such as blood as a reference element for a quantitative analysis of a mineral contained in the biological fluid, it became possible to conduct a quantitative analysis of a mineral contained in a biological fluid by X-ray fluorescence analysis, and further that a content of methionine which is one of essential amino acids could be accurately obtained from a measurement value of sulfur element in the biological fluid, leading to the completion of the present invention.

That is, it is an object of the present invention to provide a method for examining a biological fluid by which quantitative examinations of various minerals and methionine, being one of essential amino acids, contained in a biological fluid can be conducted simply and accurately, and also at a low price.

In order to achieve the above object, a method for examining a biological fluid according to a first aspect of the present invention is characterized by measuring a content ratio of a mineral contained in a biological fluid of a subject which can be taken by the subject to sulfur originating in methionine contained in the biological fluid using an X-ray fluorescence analysis device, calculating contents of the sulfur and the mineral contained in the biological fluid using the measured content ratio and calibration curves previously prepared by X-ray fluorescence analysis of standard solutions of the sulfur and the mineral, and calculating a content of the methionine contained in the biological fluid on the basis of the calculated content of the sulfur.

Using the method for examining a biological fluid according to the first aspect of the present invention, the content ratio of the mineral contained in the biological fluid taken by the subject personally to the sulfur originating in methionine contained therein is measured using the X-ray fluorescence analysis device. Then, using the measured content ratio and the calibration curves, the contents of the sulfur and the mineral contained in the biological fluid are calculated. Thereafter, on the basis of the calculated content of the sulfur, the content of the methionine contained in the biological fluid is calculated. Consequently, quantitative examinations of various minerals and the methionine, being one of essential amino acids, contained in the biological fluid can be conducted without involvement by a doctor and by a professional of the examinations, resulting in extremely low-price examinations. And due to the X-ray fluorescence analysis, they can be conducted simply and accurately, and also at a low price. Since it is possible to make clear excess and shortage of intakes of various minerals and the methionine contained in the biological fluid, it is possible to easily grasp the state of health of the subject.

According to a trial calculation by the inventors of the present invention, by this examination method, it becomes possible to conduct examinations of 12 elements, for example, at about 3,000 yen, that is, about 250 yen per mineral (element). By allowing this examination method to come into wide use, it becomes possible to conduct appropriate nutritional counseling or diet counseling on a large number of subjects, and it becomes possible to make preventive medical care aiming at maintenance/promotion of health innovatively widespread.

In the examination method according to the present invention, for quantitative analyses of elements contained in the biological fluid by the X-ray fluorescence analysis, sulfur originating in methionine, being an essential amino acid, contained in the biological fluid is used as a reference element of the internal standard. Here, the sulfur originating in the soluble methionine contained in the biological fluid is quite different from sulfur contained in hair, that is, sulfur originating in insoluble cystine contained in keratin.

The method for examining a biological fluid according to a second aspect of the present invention is characterized by periodically measuring a content ratio of the mineral contained in the biological fluid periodically taken from one and the same subject to the sulfur originating in methionine contained in the biological fluid, wherein a change with the passage of time in periodically calculated contents of the mineral and the methionine contained in the biological fluid is used as one of barometers for maintenance or improvement of the state of health of the subject in the method for examining a biological fluid according to the first aspect of the present invention.

In the method for examining a biological fluid according to the second aspect of the present invention, since the contents of the mineral and the like contained in the biological fluid vary between individuals, it is important to periodically measure a content ratio of the mineral contained in the biological fluid periodically taken from one and the same subject to the sulfur originating in methionine contained in the biological fluid. By using a change with the passage of time in periodically calculated contents of the mineral and the methionine contained in the biological fluid as one of barometers for maintenance or improvement of the state of health of the subject, it is possible to make more appropriate evaluations on each individual subject.

The method for examining a biological fluid according to a third aspect of the present invention is characterized by comparing the calculated contents of the mineral and the methionine contained in the biological fluid to reference contents in a person in a healthy condition so as to make evaluations regarding excess and shortage of the contents of the mineral and the methionine in the method for examining a biological fluid according to the first aspect of the present invention.

In the method for examining a biological fluid according to the third aspect of the present invention, since the calculated contents of the mineral and the methionine contained in the biological fluid and the reference contents in the person in a healthy condition are compared, it is possible to appropriately make relative evaluations regarding the excess and shortage thereof in comparison to the person in a healthy condition.

The method for examining a biological fluid according to a fourth aspect of the present invention is characterized by conducting an analysis by use of the X-ray fluorescence analysis device, using a sample prepared by taking only one or more than one drop of the biological fluid without conducting pretreatment in the method for examining a biological fluid according to any one of the first to third aspects of the present invention.

In the method for examining a biological fluid according to the fourth aspect of the present invention, by using a sample prepared by taking only one or more than one drop of the biological fluid, the burden of taking the biological fluid from the subject can be lightened. And since the analysis by use of the X-ray fluorescence analysis device is conducted without conducting pretreatment on the sample, the analysis can be simply conducted even without an advanced technique.

The method for examining a biological fluid according to a fifth aspect of the present invention is characterized by the biological fluid including at least one of blood, urine, saliva, perspiration, and tear taken by the subject personally in the method for examining a biological fluid according to any one of the first to fourth aspects of the present invention.

In the method for examining a biological fluid according to the fifth aspect of the present invention, the biological fluid includes at least one of blood, urine, saliva, perspiration, and tear taken by the subject personally. Since the subject may take the biological fluid personally, the subject does not have to go to hospital regularly for taking the biological fluid and can conveniently undergo an examination.

The method for examining a biological fluid according to a sixth aspect of the present invention is characterized by the biological fluid including at least more than one of blood, urine, saliva, perspiration, and tear taken by the subject personally in the method for examining a biological fluid according to any one of the first to fourth aspects of the present invention.

In the method for examining a biological fluid according to the sixth aspect of the present invention, the same effect as the method for examining a biological fluid according to the fifth aspect of the present invention can be obtained. And since the biological fluid includes the more than one kind of fluid, it becomes possible to detect an element, which cannot be detected or is hard to detect in one fluid, in another fluid. Therefore, the examination result can be complemented and a multifaced evaluation can be conducted.

The method for examining a biological fluid according to a seventh aspect of the present invention is characterized by the mineral including at least more than one of magnesium, phosphorus, chlorine, potassium, iron, copper, zinc, germanium, and bromine in the method for examining a biological fluid according to any one of the first to sixth aspects of the present invention.

In the method for examining a biological fluid according to the seventh aspect of the present invention, since the mineral includes at least more than one of magnesium, phosphorus, chlorine, potassium, iron, copper, zinc, germanium, and bromine, it is possible to widely conduct an evaluation regarding excess and shortage of intakes of essential minerals and the like, and an evaluation regarding in vivo contamination by taking a toxic element into the body.

BRIEF DESCRIPTION OF DRAWINGS

FIG. 13 shows an example of a report of examination results by the X-ray fluorescence analysis of minerals contained in blood of a subject and minerals contained in hair thereof in Example 4.

MODE FOR CARRYING OUT THE INVENTION

The embodiment of the method for examining a biological fluid according to the present invention is described below by reference to the Figures. The scope of the present invention is not limited to the below-described embodiment. It is needless to say that various modifications can be made as far as they do not go beyond the technical idea of the present invention, and that various examination examples/examination modes are included in the scope of the present invention.

An example of a method for examining a biological fluid according to an embodiment is described by reference to FIG. 1.

Figure 1:
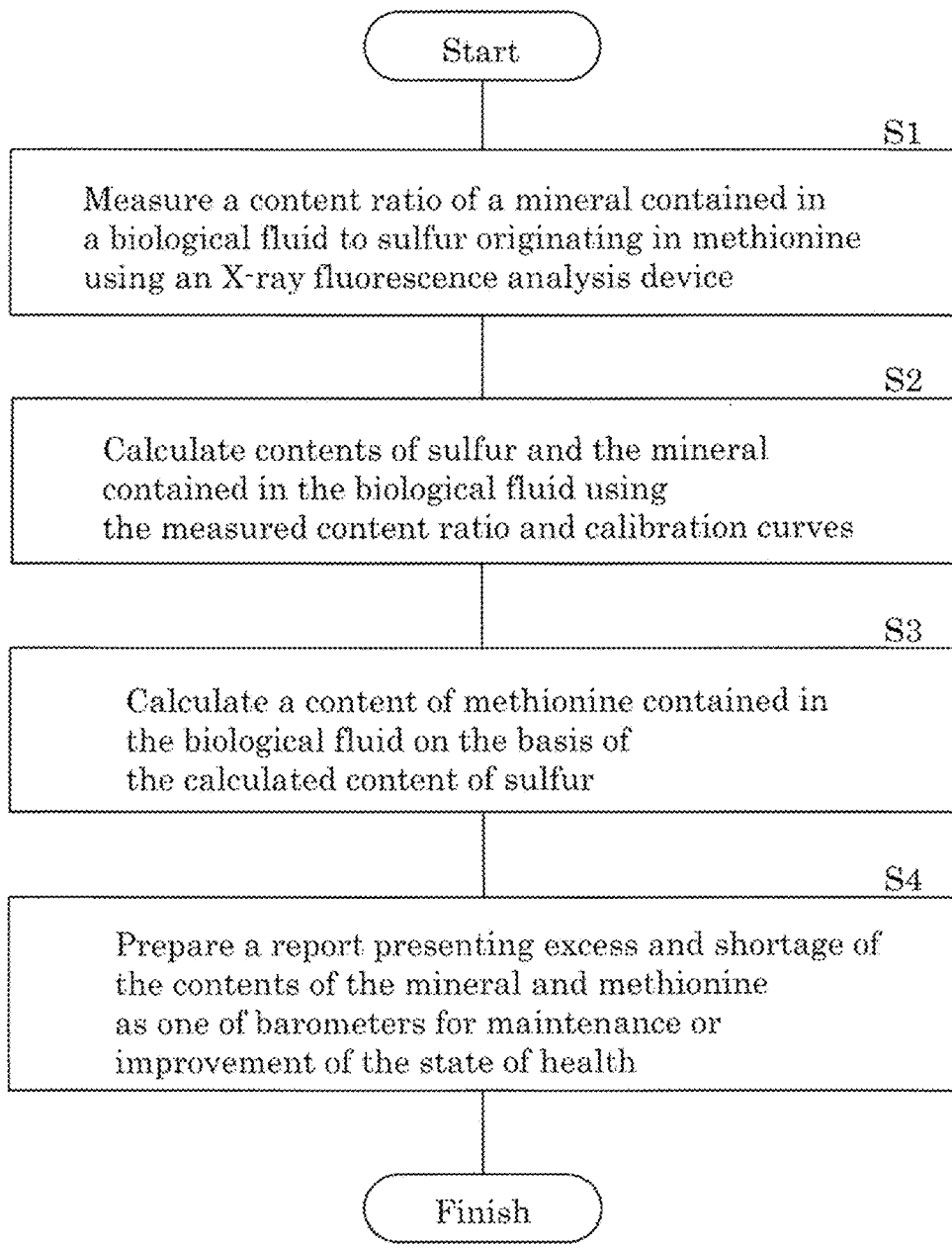
FIG. 1 is a flowchart for explaining a method for examining a biological fluid according to an embodiment of the present invention.

FIG. 1 is a flowchart for explaining the method for examining a biological fluid according to the embodiment.

In step S1, using an X-ray fluorescence analysis device, a content ratio of a mineral contained in a biological fluid of a subject which can be taken by the subject to sulfur originating in methionine contained in the biological fluid is measured. The content ratio is a ratio obtained from values such as a half value width, a height, and an area of a peak detected by X-ray fluorescence analysis, in other words, a signal ratio.

The type of the X-ray fluorescence analysis device used in this examination is not particularly limited, as far as elements to be examined can be detected thereby. For example, an energy dispersive X-ray fluorescence analysis device, a total reflection X-ray fluorescence analysis device, or a wavelength dispersive X-ray fluorescence analysis device can be used. And the device may be a desktop type, a hand-held type, or a stationary type.

The elements to be examined preferably include at least more than one of magnesium, phosphorus, sulfur, chlorine, potassium, iron, germanium, and bromine Here, the elements to be examined are not limited to these.

The biological fluid on which the X-ray fluorescence analysis is conducted may include at least one of blood, urine, saliva, perspiration, and tear taken by the subject personally.

And the biological fluid on which the X-ray fluorescence analysis is conducted may also include at least more than one of blood, urine, saliva, perspiration, and tear taken by the subject personally. These biological fluids can be taken by the subject personally, for example, using a kit for self-taking.

The analysis by use of the X-ray fluorescence analysis device may be conducted using a sample prepared by taking one or more than one drop of the biological fluid without conducting pretreatment. For example, the biological fluid may be taken on a drip material such as a piece of filter paper, a thin film, or a film Here, as these drip materials, it is desirable to use materials with few impurities.

In step S2, using the measured content ratio of each mineral and calibration curves previously prepared by the X-ray fluorescence analysis using standard solutions of sulfur and minerals (FIGS. 4-10), contents of sulfur and minerals contained in the biological fluid are calculated.

The data of the previously prepared calibration curves may be stored in the X-ray fluorescence analysis device, or a computer device connected to the X-ray fluorescence analysis device, and using these devices, by means of applying the measured content ratios to expressions of the calibration curves, respectively, the contents of sulfur and minerals contained in the biological fluid may be calculated.

In step S3, on the basis of the calculated content of the sulfur, a content of the methionine contained in the biological fluid is calculated. Since most of the sulfur contained in the biological fluid originates in methionine, the relationship between the amount of methionine in the biological fluid and that of sulfur therein is one to one.

In step S4, a report which presents excess and shortage of the calculated contents of the minerals and the methionine contained in the biological fluid as one of barometers for maintenance or improvement of the state of health is prepared. For example, a below-described report of examination results shown in FIG. 13 is prepared.

EXAMPLES

Example 1: An Examination of Blood of a Subject Using an X-Ray Fluorescence Analysis Device In this example, as elements in blood, magnesium (Mg), phosphorus (P), sulfur (S), chlorine (Cl), potassium (K), iron (Fe), and germanium (Ge) were analyzed using an X-ray fluorescence analysis device.

First of all, a sample is prepared by taking one or more than one drop of blood of a subject on a piece of filter paper. Taking of blood may be conducted by the subject personally, for example, using a commercially available kit for self-taking of blood (such as a kit for taking only one or a few drops of blood by pressing a puncture device on a finger). Then, the filter paper with the taken blood (sample) is set on the X-ray fluorescence analysis device, and the X-ray fluorescence intensity of each element contained in the blood taken on the filter paper is measured.

Figure 2:
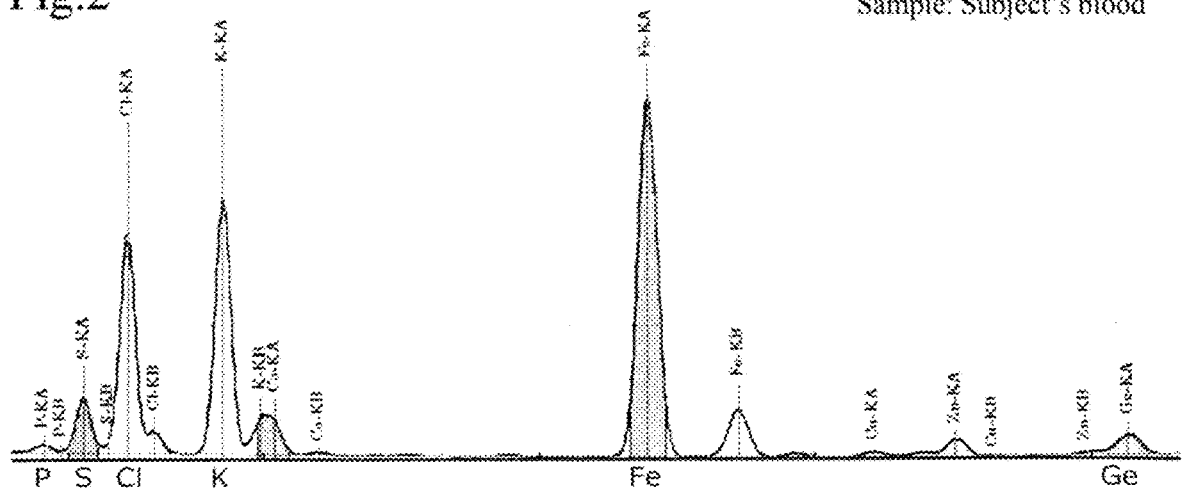
FIG. 2 is an example of a spectrum by X-ray fluorescence analysis of minerals contained in blood of a subject in Example 1.
Figure 3:
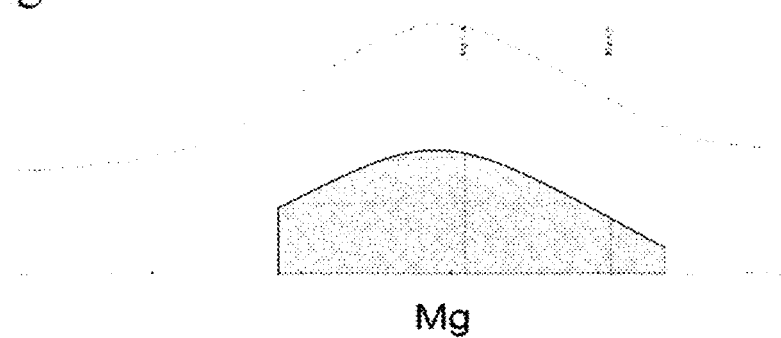
FIG. 3 is an example of a spectrum by the X-ray fluorescence analysis of a mineral (magnesium) contained in the blood of the subject in Example 1.
Figure 4:
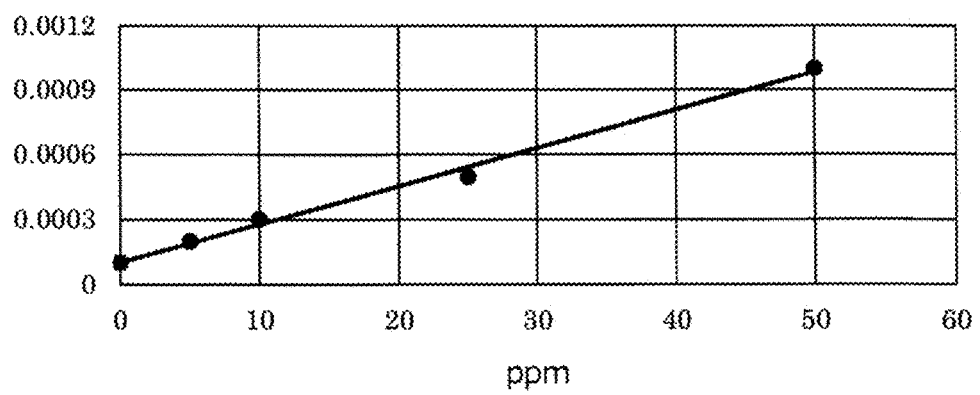
FIG. 4 is a calibration curve for obtaining a concentration of Mg in the blood of the subject from a content ratio of magnesium (Mg) to sulfur (S) in the blood of the subject in Example 1.
Figure 5:
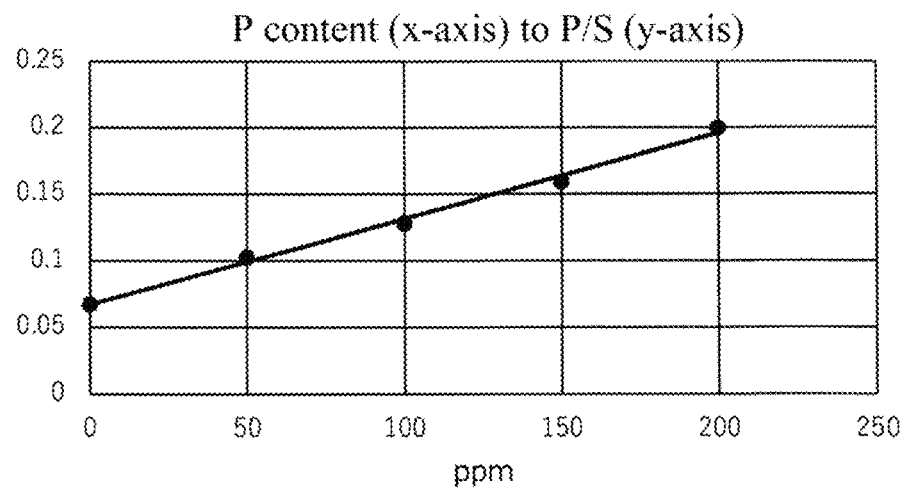
FIG. 5 is a calibration curve for obtaining a concentration of P in the blood of the subject from a content ratio of phosphorus (P) to sulfur (S) in the blood of the subject in Example 1.
Figure 6:
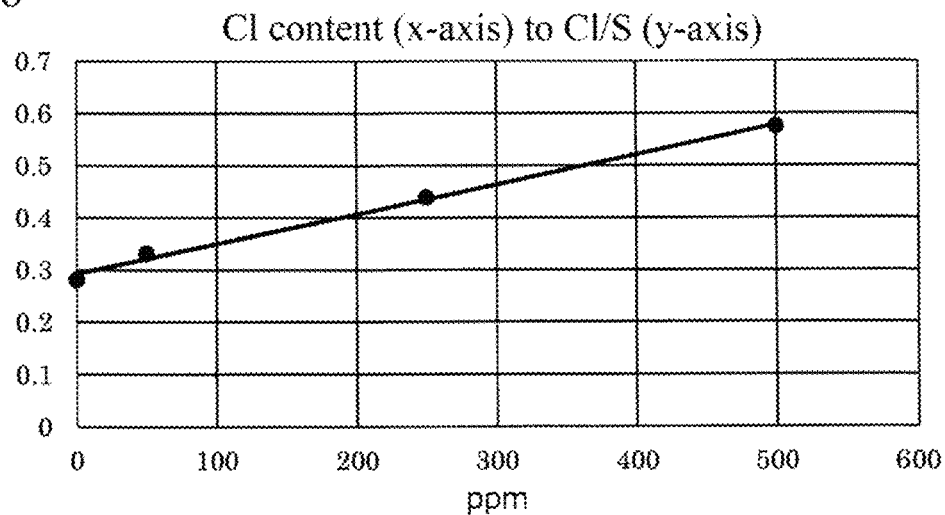
FIG. 6 is a calibration curve for obtaining a concentration of Cl in the blood of the subject from a content ratio of chlorine (Cl) to sulfur (S) in the blood of the subject in Example 1.
Figure 7:
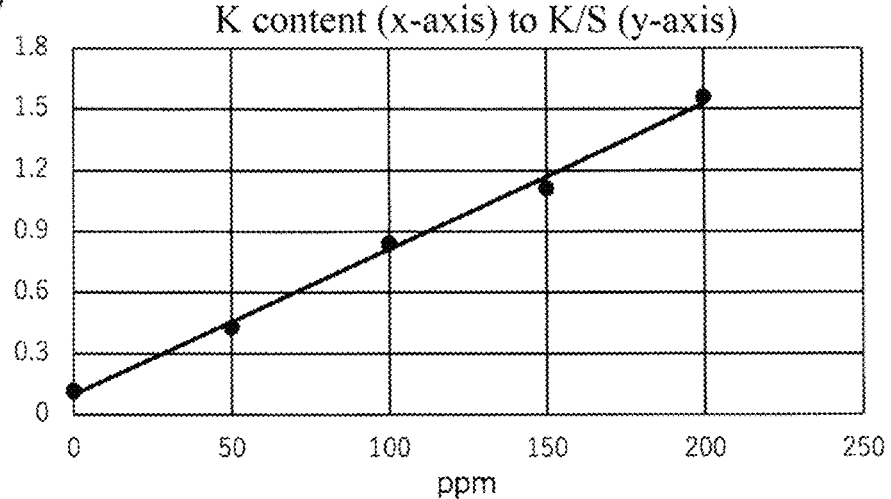
FIG. 7 is a calibration curve for obtaining a concentration of K in the blood of the subject from a content ratio of potassium (K) to sulfur (S) in the blood of the subject in Example 1.
Figure 8:
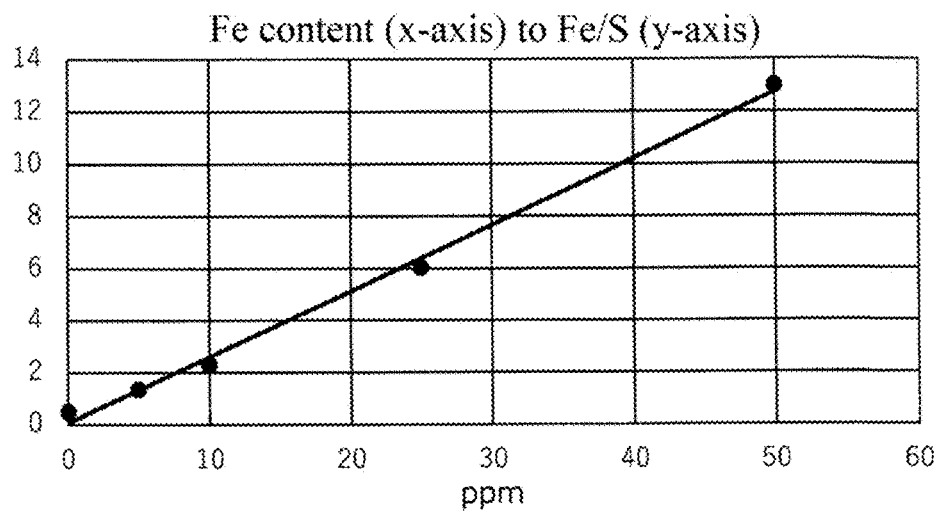
FIG. 8 is a calibration curve for obtaining a concentration of Fe in the blood of the subject from a content ratio of iron (Fe) to sulfur (S) in the blood of the subject in Example 1.
Figure 9:
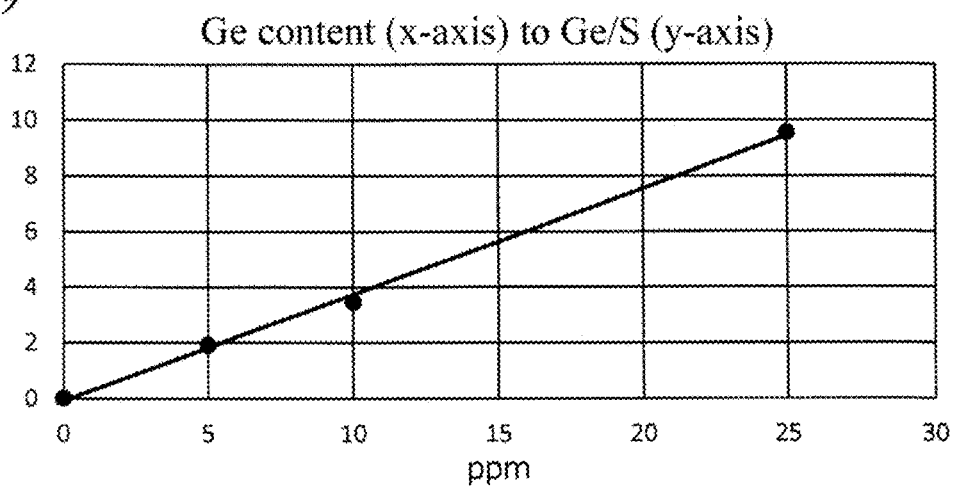
FIG. 9 is a calibration curve for obtaining a concentration of Ge in the blood of the subject from a content ratio of germanium (Ge) to sulfur (S) in the blood of the subject in Example 1.

FIGS. 2 and 3 are examples of a spectrum by X-ray fluorescence analysis of minerals contained in the blood of the subject in Example 1. The axis of abscissa shows energy, while the axis of ordinate shows X-ray fluorescence intensity.

In the spectrum shown in FIG. 2, peaks of phosphorus (P), sulfur (S), chlorine (Cl), potassium (K), iron (Fe), and germanium (Ge) are detected. The sulfur (S) originates in methionine.

In the spectrum shown in FIG. 3, a peak of magnesium (Mg) is detected. In the case of measuring magnesium which is a light metal (a light element), since the X-ray fluorescence generated is feeble, it is preferable to produce a vacuum inside the device in order not to cause the X-ray fluorescence to be attenuated.

Then, the peak area of each element detected by the X-ray fluorescence analysis is obtained, and the content ratio of each mineral (Mg, P, Cl, K, Fe, Ge) to sulfur (S) originating in methionine (each mineral/sulfur) is measured.

By applying the measured content ratio of each mineral (Mg, P, Cl, K, Fe, Ge) to the calibration curve of each mineral (Mg, P, Cl, K, Fe, Ge) shown in FIGS. 4-9, the content (ppm) of each mineral contained in the blood is calculated. And by applying the X-ray fluorescence intensity of sulfur detected by the X-ray fluorescence analysis to the calibration curve of sulfur shown in FIG. 10, the content (ppm) of sulfur contained in the blood is calculated. On the basis of the calculated content (ppm) of sulfur, the content (ppm) of methionine contained in blood is calculated. The relationship between the amount of methionine in blood and that of sulfur therein is one to one. The above-described measurement processing or calculation processing may be conducted, for example, by the X-ray fluorescence analysis device, or a computer device connected to the X-ray fluorescence analysis device.

[Calibration Curves by X-Ray Fluorescence Analysis]

In order to prepare calibration curves, standard solutions of minerals such as magnesium (Mg), phosphorus (P), chlorine (Cl), potassium (K), iron (Fe), and germanium (Ge), and a standard solution of sulfur (S) are used.

For example, standard solutions of each mineral with three to five concentrations in consideration of the concentration range thereof in blood are prepared, and thereto, a fixed concentration of sulfur in consideration of the concentration range thereof in blood is added. Each of these prepared standard solutions of each mineral is dropped by a prescribed quantity, for example, on a piece of filter paper or a glass slide, so as to be dried. The residue after dried is analyzed using the X-ray fluorescence analysis device so as to obtain the content ratio (peak area value) of each mineral to sulfur. By indicating these content ratios on the axis of ordinate, and plotting the contents (concentrations) of each mineral in the biological fluid on the axis of abscissa, the calibration curve of each mineral is prepared.

FIGS. 4-9 show calibration curves for obtaining the content (concentration) of each mineral contained in the blood of the subject from the content ratio (relative value) of each mineral (Mg, P, Cl, K, Fe, Ge) to sulfur (S) in the blood of the subject in Example 1. It was confirmed that the calibration curves of all of the minerals had good linearity.

Figure 10:
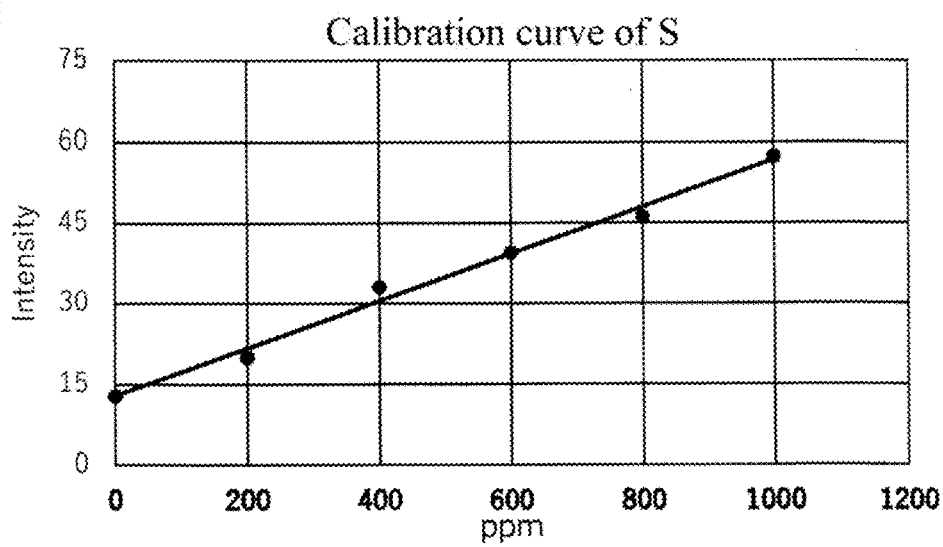
FIG. 10 is a calibration curve for obtaining a concentration of methionine from an X-ray fluorescence intensity of sulfur (S) in the blood of the subject in Example 1.

FIG. 10 shows a calibration curve for obtaining the concentration of methionine from the X-ray fluorescence intensity of sulfur (S) originating in methionine in the blood of the subject in Example 1.

For example, standard solutions of sulfur with three to five concentrations in consideration of the concentration range thereof in blood are prepared. Each of these prepared standard solutions is dropped by a prescribed quantity, for example, on a piece of filter paper or a glass slide, so as to be dried. The residue after dried is analyzed using the X-ray fluorescence analysis device so as to measure the X-ray fluorescence intensity in each concentration. By indicating the X-ray fluorescence intensities on the axis of ordinate and plotting the contents (concentrations) of sulfur on the axis of abscissa, the calibration curve is prepared. It was also confirmed that the calibration curve of sulfur shown in FIG. 10 had good linearity.

Table 1 shows measurement values of each mineral (Mg, P, Cl, K, Fe, Ge) in the blood of the subjects 1-5 in Example 1, which were calculated using the calibration curves of the minerals each shown in FIGS. 4-10.

TABLE 1

| Sub-ject | Mineral (ppm) | | | | | |
|---|---|---|---|---|---|---|
| | Magnesium | Phosphorus | Chlorine | Potassium | Iron | Germanium |
| 1 | 19.8 | 200 | 504 | 123 | 27.4 | 0.00 |
| 2 | 19.7 | 139 | 437 | 96 | 30.3 | 0.00 |
| 3 | 17.9 | 126 | 543 | 114 | 27.1 | 0.00 |

TABLE 1-continued

| Sub-ject | Mineral (ppm) | | | | | |
| --- | --- | --- | --- | --- | --- | --- |
| | Magnesium | Phosphorus | Chlorine | Potassium | Iron | Germanium |
| 4 | 18.2 | 121 | 498 | 107 | 24.7 | 0.00 |
| 5 | 18.6 | 123 | 566 | 106 | 24.7 | 1.21 |

The concentration of methionine of the subject 5, calculated using the calibration curve of sulfur shown in FIG. 10 was 1.02 ppm.

Figure 11:
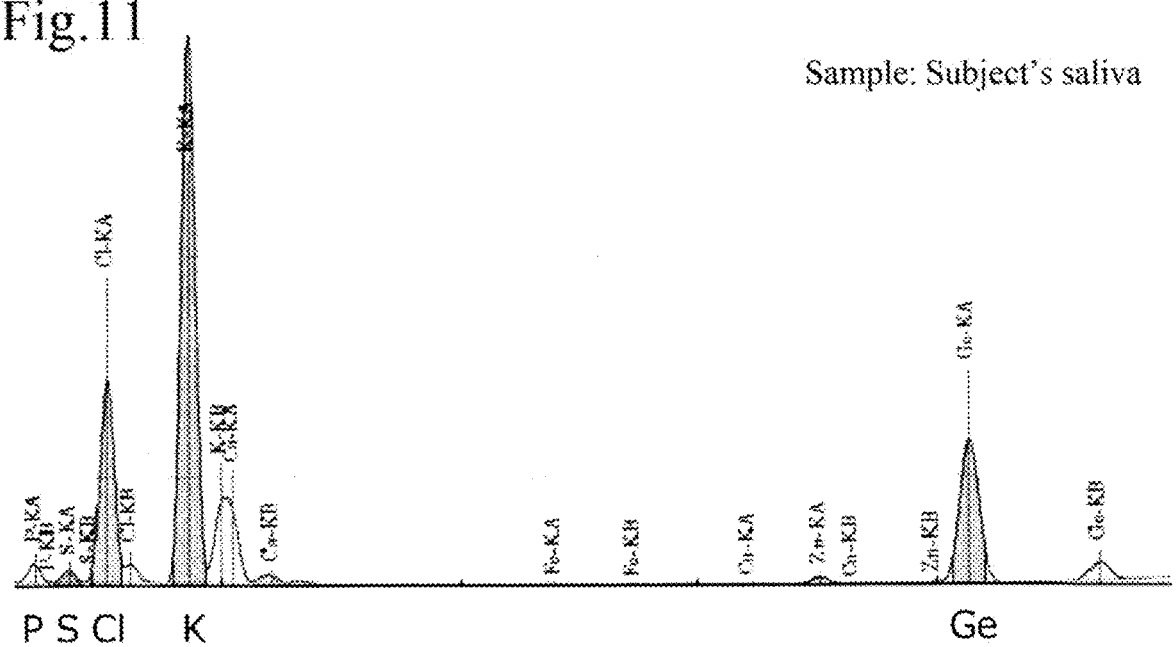
FIG. 11 is an example of a spectrum by the X-ray fluorescence analysis of minerals contained in saliva of a subject in Example 2.

Example 2: An Examination of Saliva of a Subject Using the X-Ray Fluorescence Analysis Device FIG. 11 is an example of a spectrum by the X-ray fluorescence analysis of minerals contained in saliva of a subject in Example 2. The axis of abscissa shows energy, while the axis of ordinate shows X-ray fluorescence intensity.

In the spectrum shown in FIG. 11, peaks of phosphorus (P), sulfur (S), chlorine (Cl), potassium (K), and germanium (Ge) are detected. The sulfur (S) originates in methionine. In the saliva of the subject, iron which was detected in the blood of the subject is not detected, but the other minerals are similarly detected.

Figure 12:
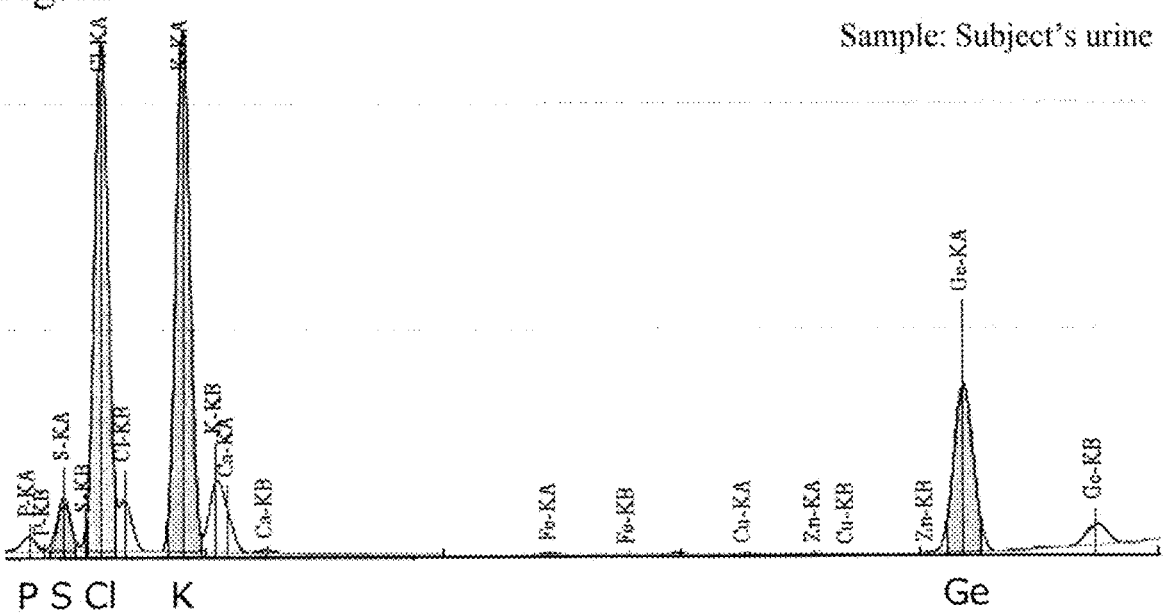
FIG. 12 is an example of a spectrum by the X-ray fluorescence analysis of minerals contained in urine of a subject in Example 3.

Example 3: An Examination of Urine of a Subject Using the X-Ray Fluorescence Analysis Device FIG. 12 is an example of a spectrum by the X-ray fluorescence analysis of minerals contained in urine of a subject in Example 3. The axis of abscissa shows energy, while the axis of ordinate shows X-ray fluorescence intensity.

In the spectrum shown in FIG. 12, peaks of phosphorus (P), sulfur (S), chlorine (Cl), potassium (K), and germanium (Ge) are detected. The sulfur (S) originates in methionine. In the urine of the subject, iron which was detected in the blood of the subject is not detected, but the other minerals are similarly detected.

In a manner similar to Example 1, the peak area of each element detected by the X-ray fluorescence analysis is obtained, and the content ratio of each mineral (Mg, P, Cl, K, Ge) to sulfur (S) originating in methionine (each mineral/sulfur) is measured.

Then, by applying the measured content ratios of each mineral (Mg, P, Cl, K, Ge) to the calibration curve of each mineral (Mg, P, Cl, K, Ge) shown in FIGS. 4-9, the contents (ppm) of each mineral contained in the saliva and the urine are calculated. And by applying the X-ray fluorescence intensities of sulfur detected by the X-ray fluorescence analysis to the calibration curve of sulfur shown in FIG. 10, the contents (ppm) of sulfur contained in the saliva and the urine are calculated. On the basis of the calculated contents (ppm) of sulfur, the contents (ppm) of methionine contained in the saliva and the urine are calculated. The relationship between the amount of methionine in the saliva or the urine, and that of sulfur therein is one to one.

Table 2 shows measurement values of each mineral (Mg, P, Cl, K, Ge) in the saliva or the urine of the subjects 1, 3 and 5 in Examples 2 and 3.

TABLE 2

| Subject | Mineral (ppm) | | | | |
| --- | --- | --- | --- | --- | --- |
| | Magnesium | Phosphorus | Chlorine | Potassium | Germanium |
| Saliva of 1 | 110 | 688 | 277 | 163 | 0.00 |
| Urine of 1 | 94 | 414 | 2962 | 262 | 0.00 |
| Saliva of 3 | 33 | 516 | 906 | 474 | 0.01 |
| Saliva of 5 | 94 | 1041 | 1808 | 842 | 26.8 |
| Urine of 5 | 36 | 268 | 1367 | 238 | 9.41 |

FIG. 13 shows an example of a report of mineral examination results by a hair and a drop of blood of a subject in Example 4.

In the "Examination Results by Blood" section, a list of mineral examination results and an evaluation comment concerning the excess and shortage of minerals are described. In the list of mineral examination results, regarding every kind of the analyzed minerals, a measurement value (ppm) and reference values (ppm) are shown. In addition, a horizontal bar graph indicating whether the measurement value is lower than the reference values, or within the reference values, or higher than those is presented.

Though it is not shown in FIG. 13, in the "Examination Results by Blood" section, as an examination result of an essential amino acid, a measurement value, reference values, and a horizontal bar graph of methionine may be described, and furthermore, an evaluation comment concerning the excess and shortage of methionine may be described.

When such report is prepared, the contents of various minerals and methionine contained in the biological fluid such as blood and the reference contents thereof in a person in a healthy condition can be compared, and therefore, it is possible to appropriately make a relative evaluation compared to the person in a healthy condition, concerning the excess and shortage of intakes of minerals and the like. Consequently, it becomes possible to use the excess and shortage of the contents of minerals and methionine contained in blood as one of barometers for maintenance or improvement of the state of health.

The report of mineral examination results shown in FIG. 13 includes the "Examination Results by Hair" section. In the "Examination Results by Hair" section, a list of mineral examination results and an evaluation comment concerning the excess and shortage of minerals are described, in a manner similar to the "Examination Results by Blood" section.

In the list of mineral examination results, similarly to the above, regarding every kind of the analyzed minerals, a measurement value (ppm) and reference values (ppm) are shown. In addition, a horizontal bar graph indicating whether the measurement value is lower than the reference values, or within the reference values, or higher than those is presented. And regarding a harmful mineral such as lead, on the basis of the measurement value, a horizontal bar graph indicating no intake, requiring care, or requiring discharge is presented. Here, as a method for examining hair, the method for conducting an examination using a preparation substrate, a hair preparation, and a hair X-ray fluorescence analysis device described in the Japanese Patent Publication No. 6460559 may be adopted.

By conducting the hair examination, too, it becomes possible to use the excess and shortage of the contents of minerals contained in the hair as one of barometers for maintenance or improvement of the state of health. And by combining at least the examination results by blood and hair, it becomes possible to allow the hair examination to be supplementary to the decision as to whether part of minerals such as calcium which is kept approximately at a fixed value because of homeostasis mechanism of blood was taken in excessively or deficiently. Hence it becomes possible to evaluate more minerals in detail. In other words, the examination by the biological fluid and the examination by hair are complementary to each other. By combining these examinations, it is possible to make use of them for preventive medical and nutritional health care such as improvement of undetected diseases or disease prevention.

Just one occasion of these examinations should not be the end. It is preferable to periodically measure the content ratios of minerals contained in a biological fluid periodically taken from one and the same subject to sulfur originating in methionine contained therein and use a change with the passage of time in the periodically calculated contents of the minerals and the methionine contained in the biological fluid as one of barometers for maintenance or improvement of the state of health of the subject.

Using the method for examining a biological fluid according to the above-described embodiment, content ratios of various minerals contained in a biological fluid such as blood, saliva, or urine taken by a subject personally to sulfur originating in methionine therein are measured using the X-ray fluorescence analysis device. Then, using the measured content ratios and the calibration curves shown in FIGS. 4-10, contents of sulfur and each mineral contained in the biological fluid are calculated. Thereafter, on the basis of the calculated content of sulfur, a content of the methionine contained in the biological fluid is calculated. By this method, quantitative examinations of various minerals and the methionine, being one of essential amino acids, contained in the biological fluid can be conducted without involvement by a doctor and by a professional of the examinations, resulting in extremely low-price examinations. And due to the X-ray fluorescence analysis, they can be conducted simply and accurately, and also at a low price. Since it is possible to make clear the excess and shortage of intakes of various minerals and methionine contained in the biological fluid, the state of health of a subject can be easily grasped.

According to a trial calculation by the inventors of the present invention, by this examination method, it becomes possible to conduct examinations of 12 elements, for example, at about 3,000 yen, that is, about 250 yen per mineral (element). By allowing this examination method to come into wide use, it becomes possible to conduct appropriate nutritional counseling or diet counseling on a large number of subjects, and it becomes possible to make preventive medical care aiming at maintenance/promotion of health innovatively widespread.

Since the contents of various minerals and the like contained in the biological fluid vary between individuals, it is important to periodically measure content ratios of various minerals contained in the biological fluid periodically taken from one and the same subject to sulfur originating in methionine contained therein. It becomes possible to use a change with the passage of time in periodically calculated contents of various minerals and methionine contained in the biological fluid as one of barometers for maintenance or improvement of the state of health of the subject. Hence it becomes possible to make more appropriate evaluations on each individual subject.

The present invention is not limited to these examples. It is needless to say that the present invention includes various kinds of embodiments within the scope which does not go beyond the technical idea according to the present invention.

INDUSTRIAL APPLICABILITY

By the method for examining a biological fluid using the X-ray fluorescence analysis device according to the present invention, it becomes possible to examine contents of various minerals and methionine, being one of essential amino acids, in a biological fluid simply and accurately, and also at a low price. By letting the subject know the excess and shortage of intakes of these minerals and methionine, it is possible to make use of them for health care of the subject so as to make preventive medical care innovatively widespread. In addition, concerning in vivo contamination by taking a toxic element into the body, it becomes possible to simply examine its influence to the body using a biological fluid.

The invention claimed is:
1. A method for examining a biological fluid, comprising the steps of:
    measuring a content ratio of a mineral contained in a biological fluid of a subject which can be taken by the subject to sulfur originating in methionine contained in the biological fluid using an X-ray fluorescence analysis device;
    calculating contents of the sulfur and the mineral contained in the biological fluid using the measured content ratio and calibration curves previously prepared by X-ray fluorescence analysis of standard solutions of the sulfur and the mineral; and
    calculating a content of the methionine contained in the biological fluid on the basis of the calculated content of the sulfur.
2. The method for examining a biological fluid according to claim 1, further comprising the step of:
    periodically measuring a content ratio of the mineral contained in the biological fluid periodically taken from one and the same subject to the sulfur originating in methionine contained in the biological fluid,
    wherein a change with the passage of time in periodically calculated contents of the mineral and the methionine contained in the biological fluid is used as one of barometers for maintenance or improvement of the state of health of the subject.
3. The method for examining a biological fluid according to claim 1, wherein
    the calculated contents of the mineral and the methionine contained in the biological fluid and reference contents in a person in a healthy condition are compared so as to make evaluations regarding excess and shortage of the contents of the mineral and the methionine.
4. The method for examining a biological fluid according to claim 1, wherein
    an analysis by use of the X-ray fluorescence analysis device is conducted using a sample prepared by taking only one or more than one drop of the biological fluid without conducting pretreatment.
5. The method for examining a biological fluid according to claim 1, wherein
    the biological fluid includes at least one of blood, urine, saliva, perspiration, and tear taken by the subject personally.

6. The method for examining a biological fluid according to claim 1, wherein
the biological fluid includes at least more than one of blood, urine, saliva, perspiration, and tear taken by the subject personally.

7. The method for examining a biological fluid according to claim 1, wherein
the mineral includes at least more than one of magnesium, phosphorus, chlorine, potassium, iron, copper, zinc, germanium, and bromine.

* * * * *